US011771121B1

(12) United States Patent
Chawla et al.

(10) Patent No.: US 11,771,121 B1
(45) Date of Patent: Oct. 3, 2023

(54) PLANT-BASED ZERO SUGAR FOOD PRODUCT AND ASSOCIATED METHOD

(71) Applicant: Chobani LLC, Norwich, NY (US)

(72) Inventors: Amrish Chawla, Twin Falls, ID (US); Sarah Allred, Twin Falls, ID (US); Zeina Jouni, Twin Falls, ID (US); Ragavendra Hari, Twin Falls, ID (US); Yucheng Hu, Twin Falls, ID (US)

(73) Assignee: Chobani LLC, Norwich, NY (US)

( * ) Notice: Subject to any disclaimer, the term of this patent is extended or adjusted under 35 U.S.C. 154(b) by 220 days.

(21) Appl. No.: 17/194,947

(22) Filed: Mar. 8, 2021

Related U.S. Application Data

(60) Provisional application No. 63/134,047, filed on Jan. 5, 2021.

(51) Int. Cl.
| | |
|---|---|
| *A23L 29/30* | (2016.01) |
| *A23L 29/00* | (2016.01) |
| *A23L 7/10* | (2016.01) |
| *A23L 29/269* | (2016.01) |

(52) U.S. Cl.
CPC ............ *A23L 29/06* (2016.08); *A23L 7/198* (2016.08); *A23L 29/272* (2016.08); *A23L 29/30* (2016.08); *C12Y 101/03004* (2013.01); *C12Y 111/01006* (2013.01); *C12Y 302/01001* (2013.01); *C12Y 302/01004* (2013.01)

(58) Field of Classification Search
CPC ......... A23L 29/06; A23L 7/198; A23L 29/30; A23L 29/272; C12Y 101/03004; C12Y 111/01006; C12Y 302/01001; C12Y 302/01004
USPC ........................................................ 426/10
See application file for complete search history.

(56) References Cited

U.S. PATENT DOCUMENTS

| | | | |
|---|---|---|---|
| 5,710,365 A | 1/1998 | Kerr et al. | |
| 5,858,449 A | 1/1999 | Crank et al. | |
| 6,147,193 A | 11/2000 | Kerr et al. | |
| 6,190,708 B1 | 2/2001 | Triantafyllou | |
| 6,395,314 B1 | 5/2002 | Whalen et al. | |
| 6,451,359 B1 | 9/2002 | Nsofor | |
| 6,451,369 B1 | 9/2002 | Triantafyllou | |
| 6,582,739 B1 | 6/2003 | Sawano et al. | |
| 6,653,451 B1 | 11/2003 | Kerr et al. | |
| 6,685,974 B2 | 2/2004 | Whalen | |
| 6,699,517 B2 | 3/2004 | Boufassa et al. | |
| 6,780,446 B2 | 8/2004 | Gao et al. | |
| 6,984,409 B2 | 1/2006 | Gao et al. | |
| 7,067,163 B2 | 6/2006 | Nsofor | |
| 7,704,540 B2 | 4/2010 | Bringe et al. | |
| 7,771,762 B2 | 8/2010 | Gao et al. | |
| 8,333,986 B2 | 12/2012 | Chen et al. | |
| 8,337,880 B2 | 12/2012 | Chen et al. | |
| 8,449,935 B2 | 5/2013 | Takai et al. | |
| 8,574,644 B2 | 11/2013 | Chatel et al. | |
| 8,591,970 B2 | 11/2013 | Chatel et al. | |
| 9,101,158 B2 | 8/2015 | Samoto et al. | |
| 9,131,710 B2 | 9/2015 | Boursier et al. | |
| 9,149,060 B2 | 10/2015 | Chatel et al. | |
| 9,504,272 B2 | 11/2016 | Carder et al. | |
| 9,743,684 B2 | 8/2017 | Triantafyllou | |
| 10,689,678 B2 | 6/2020 | Carder et al. | |
| 2011/0159145 A1 | 6/2011 | Alho-Lehto et al. | |
| 2013/0259973 A1 | 10/2013 | Valdez et al. | |
| 2013/0280378 A1 | 10/2013 | Aichinger et al. | |
| 2016/0081375 A1 | 3/2016 | Chatel et al. | |
| 2016/0143341 A1* | 5/2016 | Heidebach | A23L 2/54 426/10 |
| 2016/0309732 A1 | 10/2016 | Gugger et al. | |
| 2017/0318841 A1 | 11/2017 | Triantafyllou | |
| 2018/0070602 A1 | 3/2018 | Moragne et al. | |
| 2018/0213835 A1 | 8/2018 | Triantafyllou | |
| 2018/0295849 A1 | 10/2018 | Earl et al. | |
| 2019/0000100 A1 | 1/2019 | McCormick | |
| 2019/0000101 A1 | 1/2019 | Bilbao Calabuig et al. | |
| 2019/0008176 A1 | 1/2019 | Bilbao Calabuig et al. | |
| 2019/0021387 A1 | 1/2019 | Barata et al. | |
| 2019/0045826 A1 | 2/2019 | Barata et al. | |
| 2019/0274324 A1 | 9/2019 | Margolis et al. | |
| 2020/0100515 A1 | 4/2020 | Ali et al. | |
| 2020/0154753 A1 | 5/2020 | Barata et al. | |
| 2020/0229457 A1 | 7/2020 | McCormick et al. | |
| 2020/0253231 A1 | 8/2020 | Jeong et al. | |
| 2020/0260751 A1 | 8/2020 | McCormick et al. | |
| 2020/0268007 A1 | 8/2020 | McCormick et al. | |
| 2020/0268008 A1 | 8/2020 | McCormick et al. | |
| 2020/0270661 A1 | 8/2020 | Carder et al. | |
| 2020/0281224 A1 | 9/2020 | Kizer et al. | |

FOREIGN PATENT DOCUMENTS

| | | | | |
|---|---|---|---|---|
| WO | 2018209387 A1 | 11/2018 | | |
| WO | WO-2018209387 A1 * | 11/2018 | ............. | A23C 11/10 |
| WO | 2019122499 A1 | 6/2019 | | |
| WO | 2020025856 A1 | 2/2020 | | |
| WO | 2020109541 A1 | 6/2020 | | |
| WO | 2020157209 A1 | 8/2020 | | |

* cited by examiner

*Primary Examiner* — Hamid R Badr
(74) *Attorney, Agent, or Firm* — Wood Herron & Evans LLP

(57) ABSTRACT

A plant-based food product with zero sugar is provided. The plant-based food product includes an amount of water, a sugar content of between 0 wt% and 0.4 wt% referred to as having "zero sugar," and a plant-based fiber product. The plant-based fiber product includes an amount of water, a plant-based flour, an amount of plant fiber, and a plurality of enzymes comprising: an alpha amylase, a glucose oxidase, catalase, and a cellulase. The plant-based food product may be incorporated in a milk, yogurt, shake, or bar, for example.

20 Claims, 2 Drawing Sheets

PLANT-BASED ZERO SUGAR FOOD PRODUCT AND ASSOCIATED METHOD

CROSS-REFERENCE TO RELATED APPLICATION

This application is related to and claims priority to U.S. Provisional Patent Application Ser. No. 63/134,047 filed on Jan. 5, 2021, the entire contents of which are herein incorporated by reference.

TECHNICAL FIELD

This application relates to food products and methods and, in particular, relates to plant-based food products having zero sugar content and methods of manufacturing plant-based food products having zero sugar content.

BACKGROUND

In the manufacture of food products, reducing the sugar content of food products has been an increasingly appealing field of development based on the consumer marketplace and its demands. Consumer food choice decisions often turn on the sugar content in food for a variety of reasons. Popular diets, diabetic consumers, and/or other reasons have driven consumers to search for food products having lower sugar content than their predecessors. Consumption of high-sugar food products have been shown to increase a consumer's risk of developing diabetes, weight gain, and other negative health consequences. It is therefore desirable for food product manufacturers to offer alternatives and further developments for food products so as to provide a lower sugar content as an option.

Plant-based food products have historically needed to add sugar/carbohydrates to assist in improving flavoring, color, and desirability of consuming these plant-based food products. While the consumption of plant-based food products provides a significant source of many nutrients found in the plant bases of plant-based food products, as mentioned above, the addition of sugar can be detrimental to the health of the consumer and many consumers are choosing food options with reduced or zero sugar. As a result, many consumers that would otherwise be interested in plant-based food products are left with no good options in the current food product marketplace based on typical levels of sugar content in such conventional products.

Accordingly, it would be desirable to produce plant-based food products having reduced or little-to-no sugar in the final product. Of course, maintaining previously-made improvements in flavoring, color, and desirability of such food products is also an objective when making alternatives with lower sugar content.

SUMMARY

To address these and other technical problems within the conventional art, a plant-based food product with zero sugar is provided in accordance with one embodiment. The food product includes a first amount of water, a sugar content of between 0 wt% and 0.4 wt%, and a plant-based fiber product. The plant-based fiber product includes a second amount of water, a plant-based flour, and amount of plant fiber, and a plurality of enzymes. These enzymes may include at least an alpha amylase, a glucose oxidase, catalase, and a cellulase. This combination of elements making up the plant-based food product allows for various types of food products including plant-based milks, yogurts, shakes, bars, and the like with desirable flavor and coloring at least similar to conventional products with high sugar content, while substantially eliminating all sugar content from the food product. As such, the plant-based food product of this and other embodiments improves the field by providing more consumer options for such types of food products without the usual downside of a high sugar content.

In the context of this application, it will be understood that the label "zero sugar" is applied so as to mean zero or substantially zero sugar content in the final food product generated, which for the sake of example, may be defined as a sugar content of between 0 wt% and 0.4 wt%.

A plant-based food product in provided. The plant-based food product includes a first amount of water, a sugar content of between 0 wt% and 0.4 wt%, and a plant-based fiber product. The plant-based fiber product includes a second amount of water, a plant-based flour, an amount of plant fiber, and a plurality of enzymes including an alpha amylase, a glucose oxidase, catalase, and a cellulase.

In another embodiment according to the invention, the plant-based flour is oat flour.

In another embodiment according to the invention, the plant-based food product further includes an added flavoring.

In another embodiment according to the invention, the plant-based food product further includes a second plant-based flour selected from a group consisting of buckwheat flour, brown rice flour, potato flour, barley flour, oat flour, pumpkin flour, chia flour, yellow pea flour, and mixtures thereof.

In another embodiment according to the invention, the plant-based food product further includes an additional enzyme comprising a protease.

In another embodiment according to the invention, the plant-based food product further includes an additional enzyme including an acyl transferase made from Streptomyces mobaraensis bacteria using microbial fermentation.

In another embodiment according to the invention, the plant-based food product further includes maltodextrin made from starch derived from tapioca.

In another embodiment according to the invention, the plant-based food product further includes an isolate selected from soy, pea, rice, pumpkin, potato, buckwheat, chia, amaranth, brown rice, fava bean, barley, oat, mushrooms, fungi, and mixtures thereof.

In another embodiment according to the invention, the plant-based food product further includes a rice protein concentrate.

In another embodiment according to the invention, the plant-based food product further includes an oil selected from a group consisting of medium chain triglyceride oil, canola oil, and mixtures thereof.

In another embodiment according to the invention, the plant-based food product further includes gellan gum.

In another embodiment according to the invention, the plant-based food product further includes a vitamin selected from a group consisting of vitamin A, vitamin D, Vitamin E, Vitamin K, Vitamin C and Vitamin B1, B2, B3, B5, B6, B7, B9, B12, and mixtures thereof.

In another embodiment according to the invention, the plant-based food product includes a plant fiber being oat fiber.

A method of making a plant-based food product is also provided. The method includes forming a plant-based fiber product and adding water to the plant-based fiber product to form the plant-based food product. The plant-based food product formed has a sugar content of between 0 wt% and 0.4 wt%. In the described method, the plant-based fiber product is formed by adding a plant-based flour to water to form a wetted plant-flour mixture, adding an alpha amylase to the wetted plant-flour mixture, heating the wetted plant-flour mixture to a temperature between 180° F. and 200° F., cooling the wetted plant-flour mixture to a temperature between 130° F. and 150° F., adding a glucose oxidase to the wetted plant-flour mixture, adding a catalase to the wetted plant-flour mixture, clarifying the wetted plant-flour mixture into a plant fiber product and a base product, decantering the plant fiber product to form a decantered plant fiber product, mixing the decantered plant fiber product with the base product to form a buffered product, mixing the decantered plant fiber product with the base product to form a buffered product, sanitizing the buffered product by steam injection sanitation to form a sanitized buffered product, and maintaining the sanitized buffered product for a time between 3 hours and 5 hours to form the plant-based fiber product.

In another embodiment according to the invention, the plant-based flour used in the method is oat flour.

In another embodiment according to the invention, the method further includes adding an additional enzyme including a protease to the plant-based food product.

In another embodiment according to the invention, the method further includes adding an additional enzyme including an acyl transferase made from Streptomyces mobaraensis bacteria using microbial fermentation to the plant-based food product In another embodiment according to the invention, the method further includes adding maltodextrin made from starch derived from tapioca to the plant-based food product.

In another embodiment according to the invention, sanitizing the plant-based fiber product is done by a steam injection sanitation process to form a sanitized plant-based fiber product. The steam injection sanitation process includes feeding the buffered product to a direct steam injection feed tank, preheating the buffered product to a temperature of between 170° F. and 190° F., exposing the heated buffered product to direct steam injection, further raising a temperature of the buffered product to between 280° F. and 290° F., and maintained at the temperature for at least 4 seconds, and cooling the buffered product to between 40° F. and 50° F. to produce the sanitized plant-based fiber product.

In another embodiment according to the invention, the method includes fruit to the plant-based food product.

BRIEF DESCRIPTION OF THE DRAWINGS

Further features, advantages and possible applications of the present invention will be apparent from the following description in connection with the figures, in which the same reference signs are used throughout for the same or mutually corresponding elements of the invention. The accompanying drawings, which are incorporated in and constitute a part of this specification, illustrate one or more embodiments of the invention and, together with the general description given above and the detailed description given below, explain the one or more embodiments of the invention.

DETAILED DESCRIPTION

According to embodiments of the invention summarized herein, the method includes a first sub-method and a second sub-method that cooperate to form a plant-based fiber product. The plant-based fiber product is combined with water, and optionally, with additional components, to form the plant-based food product. The method described herein removes essentially all sugars from the plant-based materials resulting in a plant-based food product having zero sugar content ("zero sugar" being as defined herein). All ranges of parameters described herein include the endpoints of the ranges.

As used herein, the terms "zero sugar", "sugar free", "essentially all sugars" indicates that the product complies with FDA Regulations stating that "zero sugar" means the food must be less than 0.5 g sugar per labelled serving (i.e., 5.3 oz/150 g) and per 6 oz/170 g (the RACC or serving size for yogurt). Accordingly, food products described herein as "zero sugar", "sugar free", or free of "essentially all sugar", have, at most 0.5 g sugar per 5.3 oz or 150 g of food product or, in the case of a yogurt, 0.5 g sugar per labelled serving of 6 oz or 170 g of yogurt. In addition, food products described herein as "zero sugar", "sugar free", or free of "essentially all sugar", include a sugar content in an amount of between 0 wt% and 0.4 wt% of the food product.

Figure 1:
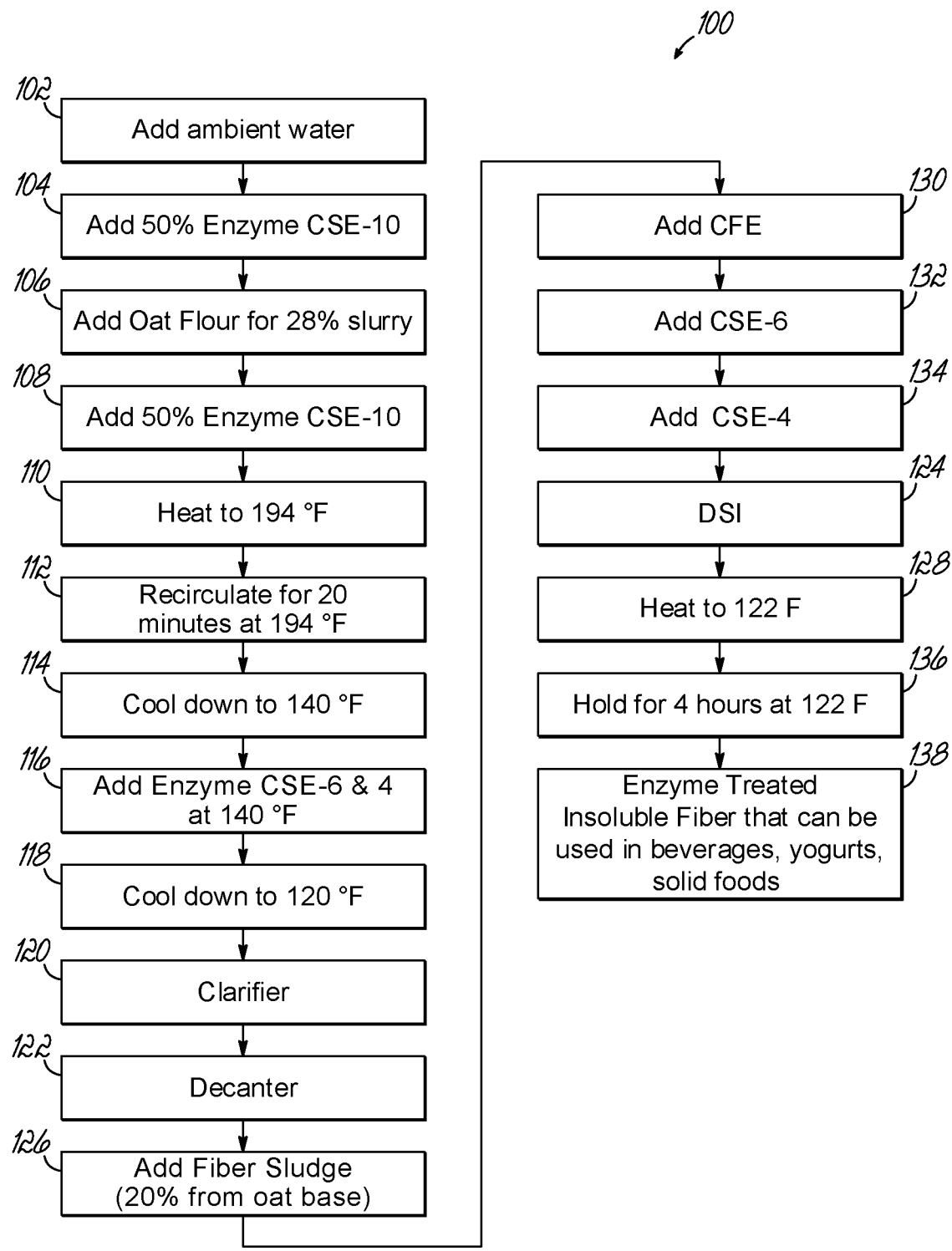
FIG. 1 is a flow chart that illustrates a first sub-method and a second sub-method of a method of manufacturing a plant-based food product.
Figure 2:
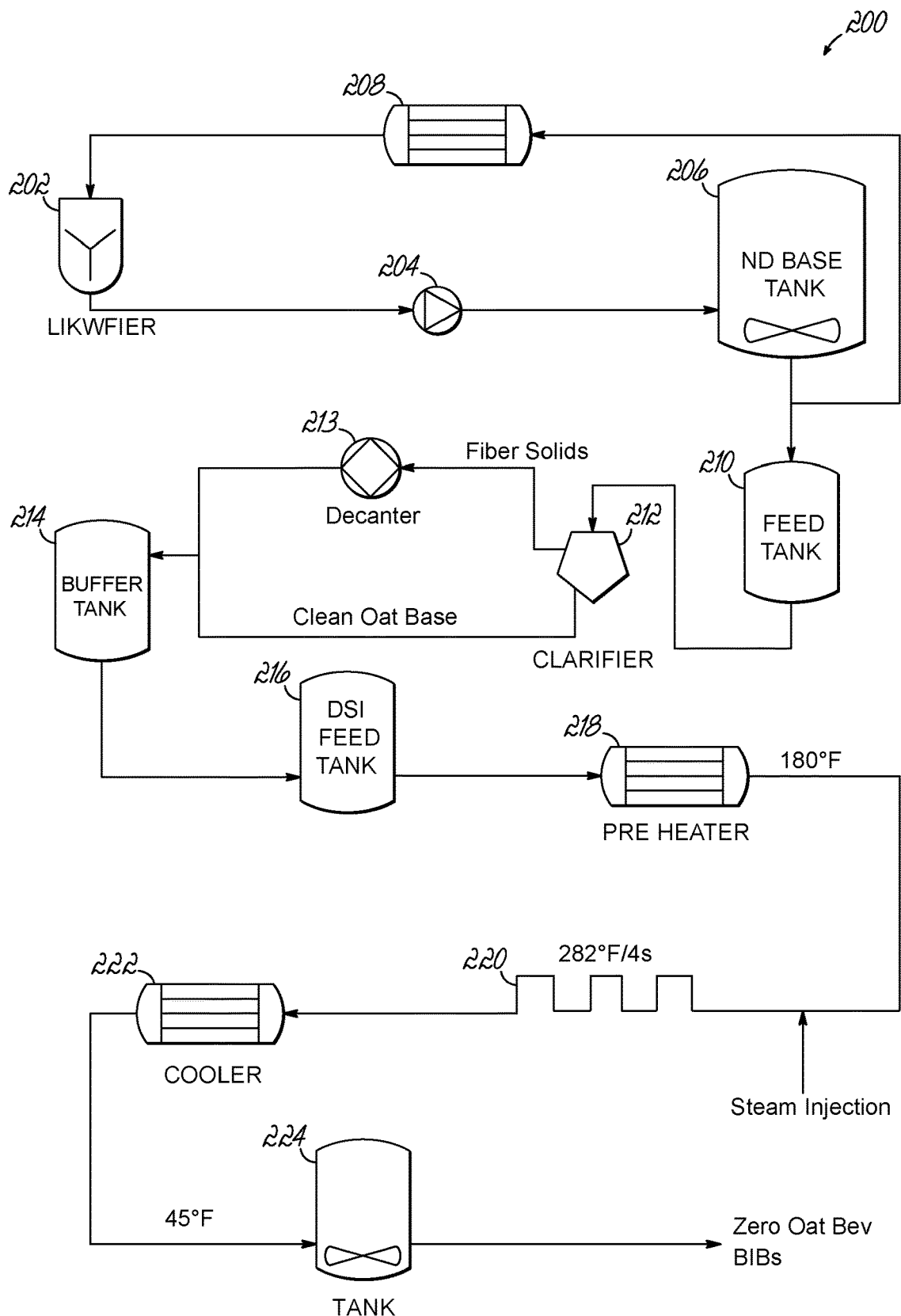
FIG. 2 is a process diagram that shows a method of manufacturing a plant-based food product.

Referring to FIGS. 1 and 2, a method 100 of manufacturing a plant-based food product is provided and a system 200 for manufacturing the plant-based food product is also provided. The method 100 includes a first sub-method and a second sub-method. The first sub-method forms a plant-based fiber product. The first sub-method includes a step 102 of providing water in an ND base tank 206. The first sub-method may optionally include step 104, step 108, or both steps 104, 108 of adding enzymes to the water provided in step 102. Furthermore, in step 106, plant-based flour is added to the water from step 102 to form a wetted plant-flour mixture. In some examples, such as the example shown in FIG. 1, the enzymes may be added stepwise. That is, a first portion of the enzymes may be added to the water, for example in step 104, before introducing the plant-based flour in step 106, and a second portion may be added to the mixture, for example in step 108, after the plant-based flour is introduced. The first portion may be, for example, about 50% of the enzymes, and the second portion may be, for example, about 50% of the enzymes, or the balance of enzymes that remains after the addition of the first portion. The enzyme added at steps 104, 108 is CSE-10, which is an alpha amylase. The CSE-10 specifically digests starch to make 3 unit carbohydrates. Specifically, the CSE-10 digests starch naturally present in oats. This naturally present starch is digested into maltotriose and other high dextrose equivalent starches. In one example, the alpha amylase used in CSE-10 is manufactured by Koninklijke DSM N.V. (Royal DSM, referred to herein as DSM) located in Heerlen, Netherlands under the product name Validase BAA 1000 L.

In step 106, plant-based flour is added to the water from step 102 which may further include the enzymes added in step 104. As described above, the plant-based flour may be oat flour. In some examples, the plant-based flour may be selected from a group consisting of oat flour, corn flour, pea flour, soy flour, buckwheat flour, wheat flour, potato flour, tapioca flour, and rice flour. The amount of plant-based flour added is between 22 and 35 wt%, preferably, the amount of plant-based flour added results in about 28 wt% of the resulting slurry to be plant-based flour.

The first sub-method further includes, in step 110, heating the wetted plant-flour mixture. In some embodiments, the heating may result in the plant-flour mixture to be heated, in step 110, to between 180° F. and 200° F., preferably to about 194° F.

The first sub-method further includes recirculating the wetted plant-flour mixture, in step 112, with or without enzymes added, for 15 minutes to 25 minutes, preferably 20 minutes, maintaining the heated temperature of the wetted plant-flour mixture throughout the recirculating process. The temperature of the wetted plant-flour mixture is maintained via the heat exchanger 208 and is mixed via liquefier 202. The recirculation is propelled by pump 204 and is fed back into the ND base tank 206.

The first sub-method further includes cooling the wetted plant-flour mixture, in step 114, to a temperature between 130° F. and 150° F., preferably 140° F.

Optionally, such as in the example method 100 shown in FIG. 1, the first sub-method may include adding additional enzymes to the cooled wetted plant-flour mixture, in step 116. These additional enzymes may be the same or different than the enzymes optionally added previously to the wetted plant-flour mixture in steps 104, 108. In some embodiments, the enzymes added at this step may be CSE-6 and CSE-4. CSE-6 is a sugar enzyme including glucose oxidase, which in one example is manufactured by DSM under the product name Delvolase GO 10. CSE-4 is a sugar enzyme including catalase, which in one example is manufactured by DSM under the product name Maxibright. In some examples, CSE-10 is a maltotriose that specifically breaks down starch included in the plant-based flour into repeating sub units having a degree of polymerization of 3 or higher. CSE-6 is an enzyme that converts any glucose produced in the above-described process into a glucuronic acid or a salt of glucuronic acid. CSE-4 is an enzyme that converts hydrogen peroxide present, such as hydrogen peroxide produced by the action of CSE-6, into oxygen. The oxygen produced by this method helps to enhance the functionality of the CSE-6 enzyme.

The first sub-method further includes further cooling the wetted plant-flour mixture to 110° F. to 130° F., preferably 120° F., in step 118. The wetted plant-flour mixture is cooled in feed tank 210.

The first sub-method further includes clarifying the wetted plant-flour mixture, in step 120, in a clarifier 212. The clarifier separates the wetted plant-flour mixture into a stream of plant fiber product and a stream of base product. As will be described below in the Examples, the base product may include water between 69 wt% and 74 wt%, plant-based flour between 26 wt% and 31 wt%, CSE-10 between 0.015 wt% and 0.0350 wt%, CSE-6 between 0.0015 wt% and 0.0035 wt%, and CSE-4 between 0.0015 wt% and 0.004 wt%. As will also be described below in the Examples, the plant fiber product includes a fiber sludge constituting between 90 wt% and 99 wt% of the plant fiber product. The fiber sludge includes between 25 wt% and 28 wt% solids after the clarifying step 120 in the clarifier 212. The plant fiber product further includes CFE-1 in an amount between 0.1 wt% and 0.25 wt%. CFE-1 is a fiber enzyme including cellulase, which in one example is manufactured by DSM under the product name Validase TRL. The plant fiber product further includes CSE-6 in an amount between 0.005 wt% and 0.01 wt%, and CSE-4 in an amount between 0.0005 wt% and 0.01 wt% of the plant fiber product. The plant fiber product further includes water in an amount between 0.73 wt % and 9.89 wt% of the plant fiber product.

The first sub-method may further include filtering the plant fiber product through a decanter 213 to form a decanted plant fiber product stream in step 122. Optionally, the first sub-method further includes adding enzymes to a tank in steps 130, 132, 134. The enzymes added at steps 130, 132, 134 may include CFE-1, CSE-6, and CSE-4. CFE-1 is a fiber enzyme including cellulase, which in one example is manufactured by DSM under the product name Validase TRL. As explained above, CSE-6 is a sugar enzyme including glucose oxidase, such as manufactured by DSM under the product name Delvolase GO 10. CSE-4 is a sugar enzyme including catalase, such as manufactured by DSM under the product name Maxibright. Optionally, in step 126, fiber solids included in the plant-based flour are treated with CFE-1, CSE-4, and CSE-6 enzymes. The addition of these enzymes enable the use of the fiber solids to be incorporated into the buffer tank 214. Step 126 occurs after step 122, and may occur is a separate tank, where the clarified and decanted insoluble plant fiber and water are mixed to form a 20-25% slurry. The slurry is then treated with CFE-1, CSE-4, and CSE-6 to form a soluble fiber solution that is then injected back into the process before step 128 to make a plant-based slurry, which may be whole oat slurry, and is then fed through the DSI process, in step 124. The plant fiber product and the base product are mixed and fed into a buffer tank 214, thus beginning the second sub-method.

The second sub-method forms a plant-based fiber product. The second sub-method includes a direct steam injection (DSI) sanitation process. The DSI sanitation process includes combining at least a portion of the decantered plant fiber product with at least a portion of the base product to form a base product mixture in, for example, a buffer tank 214, to form a buffered product. The buffered product is fed to a DSI feed tank 216. The buffered product is then preheated to a temperature of between 170° F. and 190° F., preferably 180° F., in preheater 218. The thus heated buffer product is then exposed to direct steam injection, further raising the temperature of the buffered product to between 280° F. and 290° F., preferably 282° F., in the steam heater 220. The buffered product is maintained at the steam-heated temperature for at least 4 seconds. The heated buffered product may be allowed to cool, and then reheated to between 280° F. and 290° F., preferably 282° F., in steam heater 220. This heating/cooling cycle may be repeated as necessary to form a sanitized buffered product. The sanitized buffered product is cooled to between 40° F. and 50° F., preferably 45° F., in cooler 222, and fed into a tank 224, and accordingly ending the DSI sanitation process in step 124.

The tank 224 mixture is permitted to stand in step 136, optionally with maintaining the temperature of the tank mixture, for a time between 3 hours and 5 hours, preferably 4 hours, and forms the plant-based fiber product, in step 138. In the tank 224, the sanitized buffered product is heated to between 110° F. and 130° F., preferably 122° F., in step 128.

The plant-based fiber product is formed into the plant-based food product by adding at least water to the plant-based fiber product. Optionally, further additions may be added to the plant-based fiber product, such as flavorings (artificial or natural), plant protein isolates and/or concentrates such as from soy, pea, rice, pumpkin, potato, buckwheat, chia, amaranth, brown rice, fava bean, barley, oat, mushrooms, fungi, and mixtures thereof, enzymes, plant-based flour such as buckwheat flour, brown rice flour, potato flour, barley flour, oat flour, pumpkin flour, chia flour, yellow pea flour, and mixtures thereof, oils such as medium chain triglyceride (MCT) oil which include two or three fatty acids, canola oil, and mixtures thereof, gellan gum, and vitamins such as Vitamin A, Vitamin D, Vitamin E, Vitamin K, Vitamin C and Vitamin B1, B2, B3, B5, B6, B7, B9, B12, and mixtures thereof. The fatty acids included in the MCT oil include carbon chain moieties having carbon chains of between 6 and 13 carbon atoms, and may include branched or non-branched carbon chains, saturated or unsaturated carbon chains, or combinations thereof. The enzyme additions used to form the plant-based food product may include CPE-1 and CPE-4. CPE-1 protein enzyme including a protease enzyme, which in one example is manufactured by DSM under the product name MaxiPro CPP. CPE-4 is a mixture of a protein enzyme including an acyl transferase made from Streptomyces mobaraensis bacteria using microbial fermentation and maltodextrin made from starch derived from tapioca. In one example, the CPE-4 used in the method 100 is manufactured by Ajinomoto Co., Inc. located in Chuo City, Tokyo, Japan. CPE-4, as manufactured by Ajinomoto, is marketed under the product name TI. Alternatively or in addition, other additions may be added to the plant-based fiber product and water, such as fruits—pureed, extracts, or concentrates—and/or a blend of vitamins and minerals, including Vitamins A, C, D, E, K, B1 (thiamine), B2 (riboflavin), B3 (niacin), B5 (pantothenic acid), B6, B7 (biotin), B12 (cyanocobalamin), B9 (folic acid and B9), choline, carnitine and calcium, phosphorus, sodium, potassium, magnesium, manganese, sulfur, chloride, iron, iodine, fluoride, zinc, copper, selenium, chromium, cobalt, and combinations thereof. The plant-based food product may be any of a drink, milk, yogurt, or the like, advantageously having zero sugar content, that is, sugar content between 0 wt % and 0.4 wt%.

The plant-based food product includes the plant-based fiber product and at least water. Optional additions may be included in the plant-based food product, such as various fruit and food flavorings and spices including strawberry, banana, blueberry, cherry, raspberry, peach, chocolate, vanilla, cinnamon, peppermint, and combinations thereof, plant protein isolates and/or concentrates such as from soy, pea, rice, pumpkin, potato, buckwheat, chia, amaranth, brown rice, fava bean, barley, oat, mushrooms, fungi, and mixtures thereof, enzymes, plant-based flour such as buckwheat flour, brown rice flour, potato flour, barley flour, oat flour, pumpkin flour, chia flour, yellow pea flour, and mixtures thereof, oils such as MCT oil, canola oil, and mixtures thereof, gellan gum, and vitamins such as vitamin A, vitamin D, Vitamin E, Vitamin K, Vitamin C and Vitamin B1, B2, B3, B5, B6, B7, B9, B12, and mixtures thereof. Alternatively or in addition, the plant-based food product may include fruits—pureed, extracts, or concentrates—and/or a blend of vitamins and minerals, including Vitamins A, C, D, E, K, B1 (thiamine), B2 (riboflavin), B3 (niacin), B5 (pantothenic acid), B6, B7 (biotin), B12 (cyanocobalamin), B9 (folic acid and B9), choline, carnitine and calcium, phosphorus, sodium, potassium, magnesium, manganese, sulfur, chloride, iron, iodine, fluoride, zinc, copper, selenium, chromium, cobalt, and combinations thereof.

EXAMPLES

An example formulation of the base product has the formulation as shown in Table 1. The values shown in Table 1 are meant to include a range of values. For example, each of the components listed in Table 1 may be included in the plant-based food product in a weight percentage of between the value listed in the "Wt% of final product, Low" column and the "Wt% of final product, High" column. This is true regardless of whether the value in the "Wt% of final product, Low" column is greater than or less than the value of the "Wt% of final product, High" column:

TABLE 1

FORMULATION OF EXAMPLE BASE PRODUCT

| Component | Wt % of final product, Low | Wt % of final product High |
|---|---|---|
| Water | 69 | 74 |
| Oat Flour | 31 | 26 |
| CSE-10 | 0.015 | 0.0350 |
| CSE-6 | 0.0015 | 0.0035 |
| CSE-4 | 0.0015 | 0.004 |

An example formulation of the plant fiber product has the formulation as shown in Table 2. The values shown in Table 2 are meant to include a range of values. For example, each of the components listed in Table 2 may be included in the plant-based food product in a weight percentage of between the value listed in the "Wt% of final product, Low" column and the "Wt% of final product, High" column. This is true regardless of whether the value in the "Wt% of final product, Low" column is greater than or less than the value of the "Wt% of final product, High" column:

TABLE 2

FORMULATION OF EXAMPLE PLANT FIBER PRODUCT

| Component | Wt % of final product, Low | Wt % of final product High |
|---|---|---|
| Fiber Sludge 25-28% Solids after clarifier | 90 | 99 |
| CFE-1 | 0.1 | 0.25 |
| CSE-6 | 0.005 | 0.01 |
| CSE-4 | 0.005 | 0.01 |
| Water | 9.89 | 0.73 |

The base product described in Table 1 and the plant fiber product described in Table 2 are combined upon entering the DSI sanitation step 124, as described above to form a plant-based fiber product. The plant-based fiber product is used in the formulation of the plant-based food product. An example embodiment of the plant-based food product in the form of a plant-based milk has the formulation as shown in Table 3. The values shown in Table 3 are meant to include a range of values. For example, each of the components listed in Table 3 may be included in the plant-based food product in a weight percentage of between the value listed in the "Wt% of final product, Low" column and the "Wt% of final product, High" column. This is true regardless of whether the value in the "Wt% of final product, Low" column is greater than or less than the value of the "Wt% of final product, High" column:

TABLE 3

FORMULATION OF EXAMPLE PLANT-BASED FOOD PRODUCT

| Component | Wt % of final product, Low | Wt % of final product High |
|---|---|---|
| Water | 62 | 64 |
| CPE-1 | 0.0001 | 0.0004 |
| CPE-4 | 0.03 | 0.0015 |
| Various fruit, food flavorings, and spices including strawberry, banana, blueberry, cherry, raspberry, peach, chocolate, vanilla, cinnamon, peppermint | 0.01 | 0.005 |
| Plant-based fiber product | 28 | 31 |

TABLE 3-continued

FORMULATION OF EXAMPLE PLANT-BASED FOOD PRODUCT

| Component | Wt % of final product, Low | Wt % of final product High |
|---|---|---|
| Soy Protein Isolate | 6.5 | 3.5 |
| Pea Protein Isolate | 0.15 | 0.05 |
| Rice Protein Concentrate | 0.15 | 0.05 |
| Buckwheat Flour | 0.15 | 0.05 |
| Yellow Pea Flour | 0.15 | 0.05 |
| MCT Oil | 0.8 | 0.3 |
| Canola Oil | 2 | 1 |
| Gellan Gum | 0.09 | 0.03 |
| Vitamin A | 0.0009 | 0.0007 |
| Vitamin D | 0.00015 | 0.0001 |

The base product described in Table 1 and the plant fiber product described in Table 2 are combined upon entering the DSI sanitation step 124, as described above to form a plant-based fiber product. The plant-based fiber product is used in the formulation of the plant-based food product. Another example embodiment of the plant-based food product in the form of a plant-based nutrition shake has the formulation as shown in Table 4. The values shown in Table 4 are meant to include a range of values. For example, each of the components listed in Table 4 may be included in the plant-based food product in a weight percentage of between the value listed in the "Wt% of final product, Low" column and the "Wt% of final product, High" column. This is true regardless of whether the value in the "Wt% of final product, Low" column is greater than or less than the value of the "Wt% of final product, High" column. In Table 4, and throughout this disclosure, "fruit prep" refers to a mixture of the fruit, acidulant, stabilizers, and flavors that are mixed and processed by an ultra-high temperature process.:

TABLE 4

ALTERNATIVE FORMULATION OF EXAMPLE PLANT-BASED FOOD PRODUCT

| Component | Wt % of final product, Low | Wt % of final product High |
|---|---|---|
| Water | 15.5 | 27.5 |
| CPE-1 | 0.0004 | 0.00015 |
| CPE-4 | 0.04 | 0.015 |
| Various fruit, food flavorings, and spices including strawberry, banana, blueberry, cherry, raspberry, peach, chocolate, vanilla, cinnamon, peppermint | 0.02 | 0.015 |
| Plant-based fiber product | 32 | 28 |
| Soy Protein Isolate | 8.5 | 7.5 |
| Pea Protein Isolate | 3 | 2 |
| Rice Protein Concentrate | 2.5 | 1.5 |
| Buckwheat Flour | 1 | 0.5 |
| Yellow Pea Flour | 0.5 | 0.25 |
| MCT Oil | 1.2 | 0.4 |
| Canola Oil | 2 | 1 |
| Gellan Gum | 0.08 | 0.04 |
| Blend of minerals including calcium, phosphorus, sodium, potassium, magnesium, manganese, sulfur, chloride, iron, iodine, fluoride, zinc, copper, selenium, chromium, cobalt, and combinations thereof | 2.6 | 2.2 |
| Fruit Prep | 31 | 29 |

Notably, all of the example embodiments described above have zero sugar content. The sugar To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

What is claimed is:

1. A plant-based food product comprising:
    an amount of water;
    a sugar content of between 0 wt. % and 0.4 wt. %; and
    a plant-based fiber product comprising:
        a plant-based flour;
        an amount of plant fiber; and
        a plurality of enzymes comprising: an alpha amylase, a glucose oxidase, catalase, and a cellulase.

2. The plant-based food product of claim 1, wherein the plant-based flour is oat flour.

3. The plant-based food product of claim 1, further comprising an added flavoring.

4. The plant-based food product of claim 1, further comprising a second plant-based flour selected from a group consisting of buckwheat flour, brown rice flour, potato flour, barley flour, oat flour, pumpkin flour, chia flour, yellow pea flour, and mixtures thereof.

5. The plant-based food product of claim 1, further comprising an additional enzyme comprising a protease.

6. The plant-based food product of claim 1, further comprising an additional enzyme comprising acyl transferase made from Streptomyces mobaraensis bacteria using microbial fermentation.

7. The plant-based food product of claim 1, further comprising maltodextrin made from starch derived from tapioca.

8. The plant-based food product of claim 1, further comprising an isolate selected from the group consisting of soy, pea, rice, pumpkin, potato, buckwheat, chia, amaranth, brown rice, fava bean, barley, oat, mushrooms, fungi, and combinations thereof.

9. The plant-based food product of claim 1, further comprising a rice protein concentrate.

10. The plant-based food product of claim 1, further comprising an oil selected from the group consisting of medium chain triglyceride oil, canola oil, and combinations thereof.

11. The plant-based food product of claim 1, further comprising gellan gum.

12. The plant-based food product of claim 1, further comprising a vitamin selected from the group consisting of vitamin A, vitamin D, and combinations thereof.

13. The plant-based food product of claim 1, wherein the plant fiber is oat fiber.

14. A method of making a plant-based food product, the method comprising:
forming a plant-based fiber product by:
adding a plant-based flour to water to form a wetted plant-flour mixture;
adding an alpha amylase to the wetted plant-flour mixture;
heating the wetted plant-flour mixture to a temperature between 180° F. and 200° F.;
cooling the wetted plant-flour mixture to a temperature between 130° F. and 150° F.;
adding a glucose oxidase to the wetted plant-flour mixture;
adding a catalase to the wetted plant-flour mixture;
clarifying the wetted plant-flour mixture into a plant fiber product and a liquid product;
decanting the plant fiber product to form a decanted plant fiber product;
mixing the decanted plant fiber product with the liquid product to form a mixture;
sanitizing the mixture by steam injection sanitation to form a sanitized mixture; and
maintaining the sanitized mixture for a time between 3 hours and 5 hours to form the plant-based fiber product and
adding water, an oxidase, a catalase, and a cellulase to the plant-based fiber product to form a plant-based food product,
wherein the plant-based food product comprises a sugar content of between 0 wt. % and 0.4 wt. %.

15. The method of claim 14, wherein the plant-based flour is oat flour.

16. The method of claim 14, further comprising adding an additional enzyme comprising a protease to the plant-based food product.

17. The method of claim 14, further comprising adding an additional enzyme comprising acyl transferase made from Streptomyces mobaraensis bacteria using microbial fermentation to the plant-based food product.

18. The method of claim 14, further comprising adding maltodextrin made from starch derived from tapioca to the plant-based food product.

19. The method of claim 14, wherein sanitizing the mixture by steam injection sanitation to form the sanitized mixture comprises:
feeding the mixture to a direct steam injection feed tank;
preheating the mixture to a temperature of between 170° F. and 190° F.;
exposing the heated mixture to direct steam injection, further raising a temperature of the mixture to between 280° F. and 290° F., and maintaining at the temperature for at least 4 seconds; and
cooling the mixture to between 40° F. and 50° F. to produce the sanitized mixture.

20. The method of claim 14, further comprising adding fruit to the plant-based food product.

\* \* \* \* \*